(12) United States Patent
Cook et al.

(10) Patent No.: US 6,670,352 B2
(45) Date of Patent: *Dec. 30, 2003

(54) ANDROGENIC STEROID COMPOUNDS AND A METHOD OF MAKING AND USING THE SAME

(75) Inventors: C. Edgar Cook, Staunton, VA (US); John A. Kepler, Raleigh, NC (US); Yue-Wei Lee, Chapel Hill, NC (US); Mansukh C. Wani, Durham, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/051,172

(22) Filed: Jan. 22, 2002

(65) Prior Publication Data

US 2002/0103177 A1 Aug. 1, 2002

Related U.S. Application Data

(60) Continuation of application No. 09/328,436, filed on Jun. 9, 1999, now Pat. No. 6,369,047, which is a division of application No. 08/979,369, filed on Nov. 26, 1997, now Pat. No. 5,952,319.

(51) Int. Cl.[7] .............................................. A61K 31/56
(52) U.S. Cl. ....................................... 514/179; 552/647
(58) Field of Search ........................... 514/179; 552/647

(56) References Cited

U.S. PATENT DOCUMENTS

| 3,652,606 | A |   | 3/1972  | Baran et al. |
|-----------|---|---|---------|--------------|
| 3,846,456 | A |   | 11/1974 | Campbell et al. |
| 4,412,993 | A |   | 11/1983 | Sokolowski |
| 5,140,106 | A |   | 8/1992  | Winterfeldt et al. |
| 5,733,565 | A |   | 3/1998  | Moo-Young et al. |
| 5,952,319 | A | * | 9/1999  | Cook et al. ............... 514/179 |
| 6,369,047 | B2 | * | 4/2002  | Cook et al. ............... 514/179 |

FOREIGN PATENT DOCUMENTS

| WO | WO 93/13122 | 7/1993 |
| WO | WO 01/74839 | 10/2001 |

OTHER PUBLICATIONS

Solo et al., "7 alpha–alkyl testosterone derivatives: Synthesis and activity as androgens and as aromatase inhibitors". Steroids, vol. 40(6) pp. 603–614, 1982.

* cited by examiner

Primary Examiner—Barbara P. Badio
(74) Attorney, Agent, or Firm—Oblon, Spivak, McClelland, Maier & Neustadt, P.C.

(57) ABSTRACT

An androgenic steroid compound of the formula:

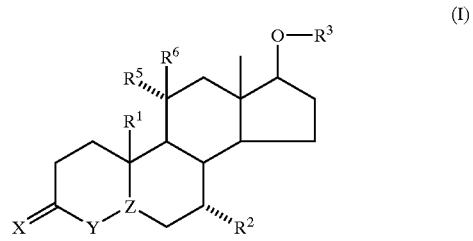

wherein:

X, Y, Z, $R^1$, $R^2$, $R^3$, $R^5$ and $R^6$ are as defined herein.

17 Claims, No Drawings

ANDROGENIC STEROID COMPOUNDS AND A METHOD OF MAKING AND USING THE SAME

This application is a continuation of application Ser. No.09/328,436, filed on Jun. 9,1999 (CPA filed May 29, 2001), now U.S. Pat. No. 6,369,047 which is a Divisional of application Ser. No. 08/979,369 filed on Nov. 26, 1997 (now U.S. Pat. No. 5,952,319).

The work leading up to the present invention was supported, at least in part, by NICHD, Contract No,. N01-HD-6-2814, 1978; and NICHD, Contract No. NO1-HD-7-2818, 1977-1979; and as such, the U.S. Government may have certain rights in the present invention.

BACKGROUND OF THE INVENTION

1. Field of the Invention

The present invention relates to androgenic steroid compounds and a method of making and using the same.

2. Discussion of the Background

Testosterone is the principal male hormone and is required for the development and maintenance of secondary sexual characteristics, libido and spermatogenesis. Testosterone also has anabolic properties, in promoting muscle growth and maintenance. Lower than normal testosterone levels in men have been associated with low energy, frailty, depression, decreased libido, weakness, lethargy, loss of lean body and bone mass and impotence. A second androgen, dihydrotestosterone (DHT), is produced from testosterone. DHT is a potent androgen. It is believed to be responsible for prostate growth and inhibitors of the enzyme that forms it have been used to treat prostatic hypertrophy and benign prostate hyperplasia.

Testosterone is rapidly metabolized in the body. Since the liver metabolizes most orally administered testosterone before it reaches the systemic blood circulation, large oral doses are necessary in order to have the desired effect. To some extent, this difficulty may be overcome by using the drug in the form of a fatty acid ester and administering the same by intramuscular injection, nevertheless, doses of 200 mg must still be given at weekly or bi-weekly intervals. Although testosterone can be administered by skin patch, large patches must be used due to low activity and rapid metabolism. Recently, a permeation-enhanced back patch was reported, however, this still requires the use of two large, i.e. 37 cm$^2$ patches for a total area of 11.5 in$^2$ or about 30% more area than an ordinary playing card.

Hence, a need exists for an androgenic compound that has enhanced potency relative to testosterone, which would permit more facile procedures for administration, such as the use of smaller skin patches, implantable devices or even oral or buccal administration.

SUMMARY OF THE INVENTION

In accordance with the present invention, androgenic steroid compounds are provided which exhibit enhanced activity relative to testosterone.

The present invention also provides a method of making the androgenic steroid compounds.

The present invention also provides a therapeutic method for the administration of the present androgenic steroid compounds and compositions containing the same.

Accordingly, the above objectives and others are provided by an androgenic steroid compound having the ring numbering system and the formula (I):

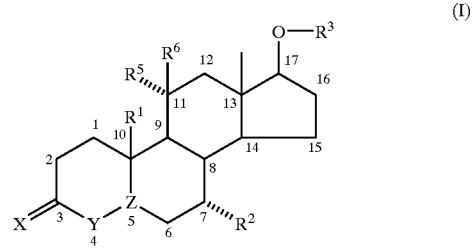

(I)

wherein $R^1$ is H or lower alkyl;

Y—Z is CH=C or CH$_2$—CH, wherein H is α to the rings, or Y—CH wherein H is α to the rings and Y is S, O, or NR$^{10}$, wherein $R^{10}$ is H or lower alkyl;

$R^2$ is an α-substituent which is unsubstituted lower alkyl or fluoro-substituted lower alkyl;

$R^3$ is C$_1$–C$_8$ alkyl, or C$_2$–C$_8$ alkenyl or alkynyl, which are optionally substituted; or $R^3$ is C$_4$–C$_8$ cycloalkyl which is unsubstituted or substituted; or $R^3$ is C$_6$–C$_{18}$ aryl which is unsubstituted or substituted; or $R^3$ is a 5- to 15-membered heterocycle which is unsubstituted or substituted, and further wherein any of the above may be substituted with 1 to 3 heteroatoms or 1 to 5 halogen atoms or both; or $R^3$ is H or an acyl group (CO)—$R^4$, wherein $R^4$ is C$_1$–C$_{18}$ alkyl, or C$_2$–C$_{18}$ alkenyl or alkynyl which are optionally substituted; or $R^4$ is C$_4$–C$_{18}$ cycloalkyl or substituted cycloalkyl; or $R^4$ is C$_6$–C$_{18}$ aryl or substituted aryl; or $R^4$ is a 5- to 15-membered heterocycle or substituted heterocycle, and wherein $R^4$ may be optionally substituted with 1 to 3 heteroatoms or 1 to 5 halogen atoms or both;

$R^5$ is α-H, and $R^6$ is β-lower alkyl, alkenyl or alkynyl which are optionally substituted; or $R^5R^6$ is =CH$_2$; and X is O, H$_2$, (H, OH) or (H$_1$, OCOR$^4$), wherein $R^4$ is as defined above; or X is (H, OR$^3$), wherein $R^3$ is as defined above; or X is NOR$^7$, wherein $R^7$ is H or C$_1$–C$_8$ alkyl, or C$_2$–C$_8$ alkenyl or alkynyl which are optionally substituted; or $R^7$ is C$_4$–C$_8$ cycloalkyl or substituted cycloalkyl; or $R^7$ is C$_6$–C$_{18}$ aryl or substituted aryl; or $R^7$ is a 5- to 15-membered heterocycle or substituted heterocycle, and $R^7$ may be optionally substituted with 1 to 3 heteroatoms or 1 to 5 halogen atoms or both; or X is (OR$^8$, OR$^9$), where $R^8$ and $R^9$ are lower alkyl or (OR$^8$, OR$^9$) is a cyclic structure containing 2 to 3 carbon atoms, optionally substituted with lower alkyl, or 1 or 2 heteroatoms or halogens.

DETAILED DESCRIPTION OF THE PREFERRED EMBODIMENTS

In accordance with the present invention, certain androgenic steroid compounds are provided which exhibit surprisingly enhanced activity relative to testosterone. Due to the enhanced potency of the present compounds, their administration is quite facile. For example, by virtue of the present invention, it is now possible to significantly reduce the size of skin patches required for skin administration. This also provides greater flexibility in the design of the patches. Moreover, the compounds of the present invention exhibit long-lasting effects after injection.

Generally, the present invention provides androgenic steroid compounds of the formula (I):

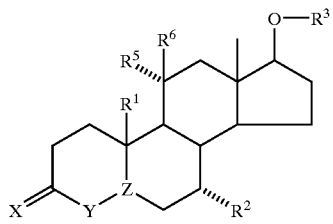

(I)

wherein:
R¹ is H or lower alkyl;
Y—Z is CH=C or CH₂—CH, wherein H is α to the rings; or Y—CH wherein H is α to the rings and Y is S, O, or NR¹⁰, wherein R¹⁰ is H or lower alkyl;
R² is an α-substituent which is unsubstituted lower alkyl or fluoro-substituted lower alkyl;
R³ is C₁–C₈ alkyl, or C₂–C₈ alkenyl or alkynyl which are optionally substituted; or R³ is C₄–C₈ cycloalkyl which is unsubstituted or substituted; or R³ is C₆–C₁₈ aryl which is unsubstituted or substituted; or R³ is a 5- to 15-membered heterocycle which is unsubstituted or substituted, and further wherein any of the above may be further substituted with 1 to 3 heteroatoms or 1 to 5 halogen atoms or both; or
R³ is H or an acyl group (CO)—R⁴, wherein R⁴ is C₁–C₁₈alkyl, or C₂–C₁₈ alkenyl or alkynyl which are optionally substituted; or R⁴ is C₄–C₁₈ cycloalkyl or substituted cycloalkyl; or R⁴ is C₆–C₁₈ aryl or substituted aryl; or R⁴ is a 5- to 15-membered heterocycle or substituted heterocycle, and wherein R⁴ may be optionally substituted with 1 to 3 heteroatoms or 1 to 5 halogen atoms or both;
R⁵ is α-H, and R⁶ is β-lower alkyl, alkenyl or alkynyl which are optionally substituted; or R⁵R⁶ is =CH₂; and
X is O, H₂, (H, OH) or (H, OCOR⁴), wherein R⁴ is as defined above, or X is (H, OR³), wherein R³ is as defined above; or X is NOR⁷, wherein R⁷ is H or C₁–C₈ alkyl or C₂–C₈ alkenyl or alkynyl, optionally substituted; or R₇ is C₄–C₈ cycloalkyl which is unsubstituted or which is unsubstituted or substituted, and R⁷ may be optionally substituted with 1 to 3 heteroatoms or 1 to 5 halogen atoms or both; or X is (OR⁸, OR9), where R⁸ and R⁹ are lower alkyl, or (OR⁸, OR⁹) is a cyclic structure containing 2 to 3 carbon atoms, optionally substituted with lower alkyl, or 1 to 2 heteroatoms or halogen atoms or both.

In the above formula, it is preferred that R¹ is H, R² is CH₃, R³ is H, or is an acyl group of the formula R⁴(CO), wherein R⁴ is CH₃, C₂H₅, n-C₆H₁₃, (CH₃)₂CH, cyclopentyl-CH₂—CH₂, trans-(4-n-butyl)cyclohexyl, n-C₉H₁₉, (CH₂)₂(CO)(CH₂)₅CH₃, phenyl-CH₂ or 3-pyridyl, or R³ is CH₃, C₂H₅, CH₂OCH₃, Si(CH₃)₃, CCl₃—CH(OH), or 2-tetrahydropyranyl; R⁵ is α-H and R⁶ is β-CH₃ or R⁵R⁶ is =CH₂; and X is O, NOH or NOCH₃.

More preferably, compounds such as 7α,11β-dimethyl-17β-hydroxyestr-4-en-3-one, 17β-hydroxy-7α-methyl-11-methyleneestr-4-en-3-one, 7α,11β-dimethyl-17β-heptanoyl-oxyestr-4-en-3-one, 7α,11β-dimethyl-17β-[[(2-cyclopentylethyl)carbonyl]oxy]estr-4-en-3-one, 7α,11β-dimethyl-17β-(phenacetyloxy)estr-4-en-3-one, 7α,11β-dimethyl-17β-[[(trans-4-(n-butyl)cyclohexyl)carbonyl]oxy]estr-4-en-3-one, and 7α,11β-dimethyl-17β-hydroxy-5α-estran-3-one may be mentioned.

As used herein, the terms "lower alkyl" and "lower alkoxy" mean from 1 to 8 carbons, preferably from 1 to 4 carbons and specifically methyl, ethyl, propyl, iso-propyl, n-butyl, sec-butyl or tert-butyl. The term "cycloalkyl" means a cyclic structure which may have one or more rings, fused or unfused, each ring containing 4 to 12 carbon atoms, and optionally containing double bond unsaturation. For example, single rings may include from 4 to 12 carbons, such as cyclobutyl, cyclopentyl, cyclohexyl, cycloheptyl, cyclooctyl, cyclononyl, cyclodecyl, cycloundecyl, or cyclododecyl.

The term "heteroatom" means oxygen, nitrogen, sulfur or silicon atoms.

Further, where used the term "substituted" generally means substituted with lower alkyl or alkoxy as defined herein, and preferably with 1 to 4 carbons, or with halogen, such as fluoro or with both.

As used herein, the terms "lower alkenyl" and "lower alkynyl" mean, in general, those groups with 2 to 8, preferably 1 to 4, carbons. Examples of "lower alkenyl" are vinyl, propenyl, butenyl, pentenyl, hexenyl, heptenyl or octenyl. Examples of "lower alkynyl" are ethynyl, propynyl, butynyl, pentynyl, hexynyl, heptynyl or octynyl.

Additionally, as used herein, "heterocycle" means any heterocyclic ring system containing 1 to 3 heteroatoms, such as pyrazine, pyrimidine, pyridazine, imidazole, isoxazoline, pyrazole, pyrazolidine or thiazoline. By 5- to 15-membered is meant that the total number of structural core atoms in the ring system is 5- to 15. This includes carbon atoms and the heteroatoms in the ring system, and substituents, and not, of course, hydrogen. Furthermore, the ring system may consist of a single ring, as exemplified above, or may consist of fused ring systems, such as, for example, quinoline, or multiple unfused rings, such as, for example, 2-phenylpyridine.

As may be seen from the formula above, the androgenic steroid compounds of the present invention generally contain a 7α-group in conjunction with an 11β-methyl group or an 11-methylene group. Generally, moieties R¹ and —OR³ of formula (I) are each in the β-orientation.

Further, the present compounds are generally characterized by a 17β-hydroxyl, ether or ester group. Generally, the 17β-ester or ether compounds may be considered to be pro-drugs of the 17β-hydroxy compounds. The former are presumably metabolized or hydrolyzed in vivo to form the latter.

Moreover, the present compounds are further generally characterized by a 3-keto, -oxime or -methoxime group.

Generally, R² is lower alkyl or lower alkyl substituted by fluorine.

R³ is H or an acyl group (CO)—R⁴, wherein R⁴ is C₁–C₁₈ alkyl, or C₂–C₁₃ alkenyl or alkynyl which are optionally substituted; or R⁴ is C₄–C₁₈ cycloalkyl or substituted cycloallyl; or R⁴ is C₄–C₁₈ aryl or substituted aryl; or R⁴ is a 5- to 15-membered heterocycle or substituted heterocycle, and wherein each of the above may be optionally substituted with 1 to 3 heteroatoms or 1 to 5 halogen atoms or both; or R⁶ is lower alkyl, lower alkenyl or lower alkynyl.

X is O, H₂, (H, OH) or (H, OCOR⁴), wherein R⁴ is as defined above; or X is (H, OR³), wherein R³ is as defined above; or X is NOR⁷, wherein R⁷ is H or C₁–C₈ alkyl, or C₂–C₁₈ alkenyl or alkynyl which are optionally substituted; or R⁷ is C₄–C₈ cycloalkyl or substituted cycloalkyl; or R⁷ is C₆–C₁₈ aryl or substituted aryl; or R⁷ is a 5- to 15-membered heterocycle or substituted heteorcycle, and $R^7$ may be optionally substituted with 1 to 3 heteroatoms or 1 to 5 halogen atoms or both; or X is $(OR^8, OR^9)$, wherein $R^8$ and $R^9$ are lower alkyl, or $(OR^8, OR^9)$ is a cyclic structure containing 2 to 3 carbon atoms, optionally substituted with lower alkyl groups, or 1 or 2 heteroatoms or halogens.

For example, $(OR^8, OR^9)$ may be a cyclic group to form, with the C-3 carbon atom, a ketal, such as from ethylene glycol or 2,2-dimethyl propane-1,3-diol.

Examples of $R^3$ being (CO)—$R^4$, when $R^4$ is $C_1$–$C_{18}$ alkyl, or $C_2$-$C_{18}$, alkenyl or alkynyl which are optionally substituted and which may be (CO)—$CH_3$, (CO)—$C_2H_5$, (CO)—$C_3H_7$, (CO)—$C_4H_9$, (CO)—$C_5H_{11}$, (CO)—$C_6H_{13}$ or (CO)—$C_7H_{15}$, (CO)—$C_8H_{17}$, for alkyl, for example; (CO)—$CH_2$—CH=$CH_2$, (CO)—CH=CH—$CH_3$, (CO)—$CH_2$—CH=CH—$CH_3$, (CO)—CH=CH—$CH_2$—$CH_3$, (CO)—$CH_2$—$CH_2$—CH=CH—$CH_3$, (CO)—CH=CH—$(CH_2)_{2\text{—}CH3}$ or (CO)—CH=CH—$(CH_2)_3$—$CH_3$ for alkenyl, for example; and (CO)—C≡C—$CH_3$, (CO)—$CH_2$—C≡C—$CH_3$, (CO)—$CH_2$—$CH_2$—$CH_2$C≡C—$CH_3$, for alkynyl, for example.

Generally, substituted cycloalkyl, consistent with the above definition of "substituted" is cycloalkyl substituted by lower alkyl, lower alkoxy or halogen, preferably fluoro.

Moreover, as used herein "aryl" means carbocyclic aromatic groups, such as phenyl or naphthyl, for example, having up to 18 carbons.

Synthesis of the Androgenic Steroid Compounds

The androgenic steroid compounds of the present invention may be prepared using known reagents and reactions.

The following preparatory scheme is exemplary and provided for purposes of illustration and is not intended to be limitative.

EXAMPLE 1

By way of example, 7α,11β-dimethyl-17β-hydroxyestr-4ene-3-one may be synthesized from the known compound adrenosterone (androst-4-ene-3,11,17-trione) by the following steps, which are described below the reaction schematic. Perhaps, the most important and generally applicable feature of the synthetic process of the present invention is the introduction of the 7α-substituent ($R^2$ in formula (I)) prior to the introduction of the 11-substituent ($R^5$ and/or $R^6$ in formula (I)).

Chart A

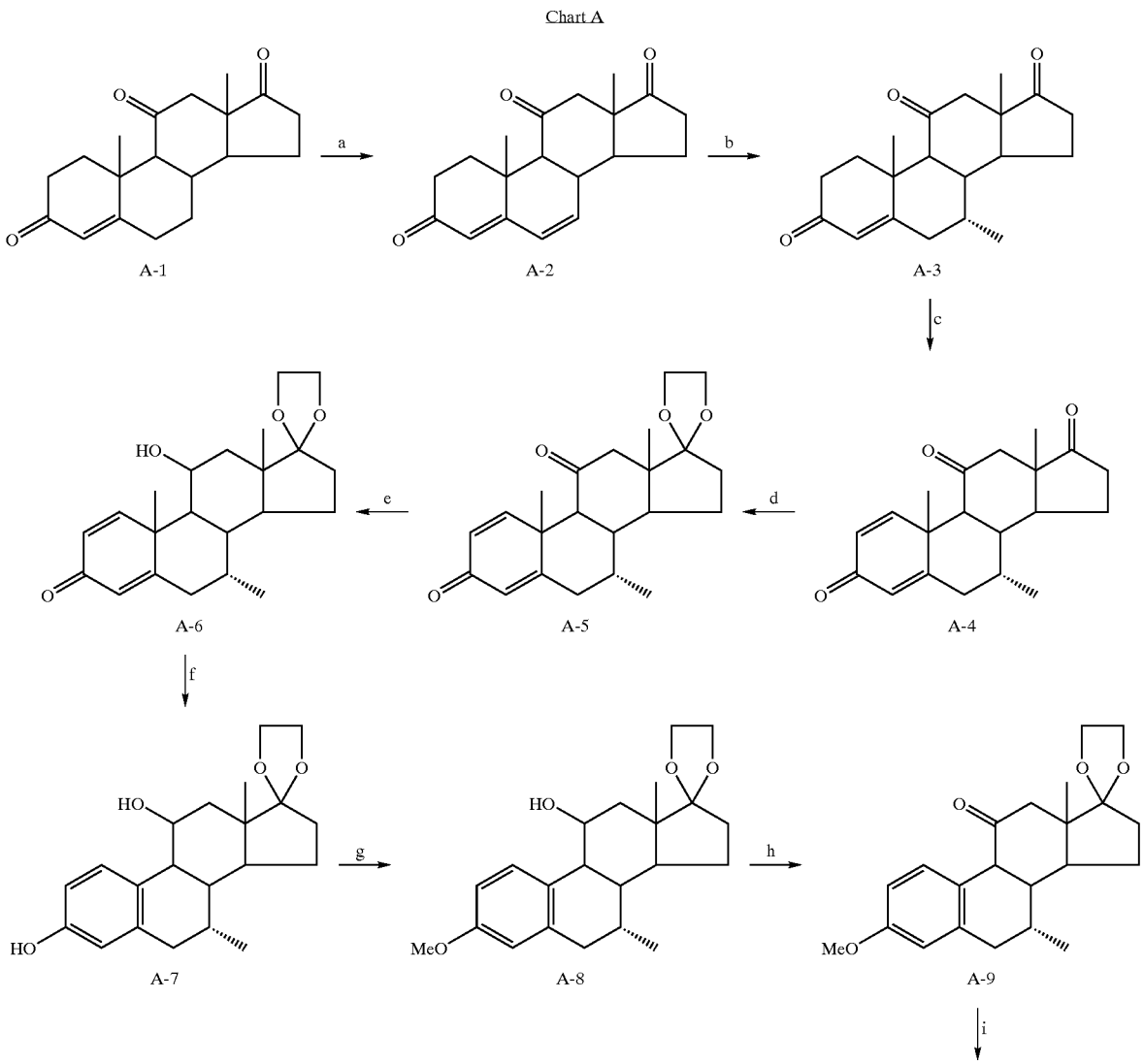

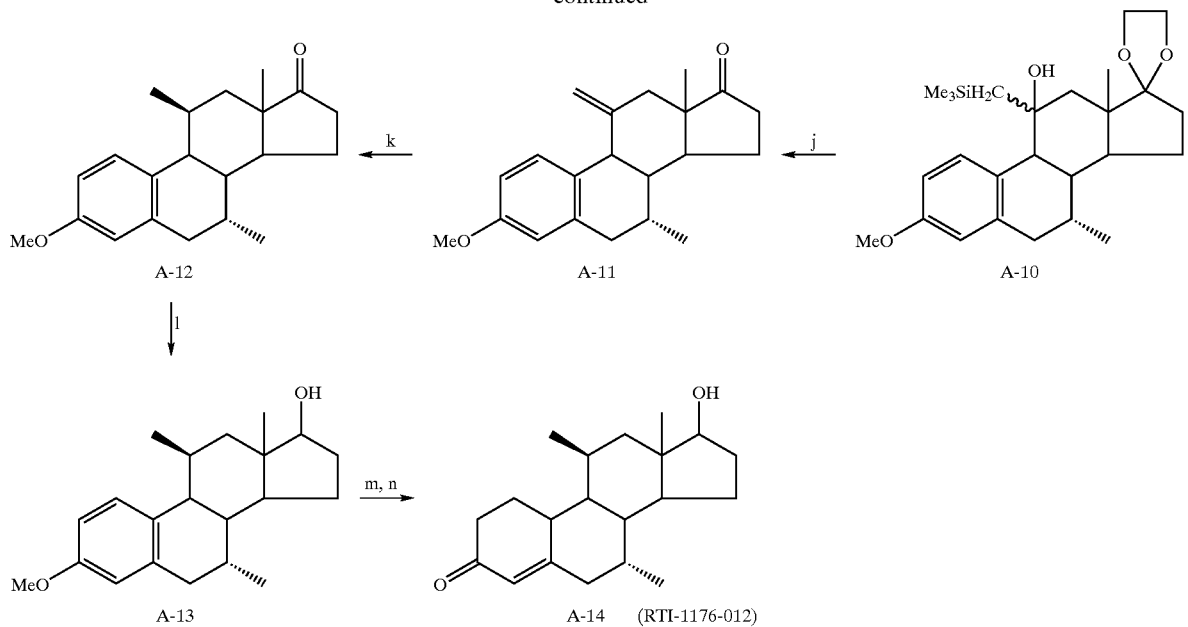

a: DDQ/HCl/Dioxane; b: Me₂CuLi, H⁺; c: DDQ/dioxane; d: ethylene glycol/TsOH; e: LiAl(OtBu)₃H; f: Li/Ph₂/Ph₂CH₂/THF; g: MeI/K₂CO₃; h: C₆H₅N•CrO₃•HCl; i: Me₃SiCH₂MgCl; j: H⁺; k: H₂/Rh/Al₂O₃(5%); l: NaBH₄; m: Li/NH₃; n: H⁺ a) introduction of a 6,7-double bond;
b) 1,6-addition of a methyl group by reaction with an organometallic reagent, followed by acid treatment;
c) introduction of a 1,2-double bond;
d) protection of the 17-ketone;
e) reduction of the 11-ketone group to an 11-hydroxy group;
f) aromatization of the A-ring to a phenol;
g) alkylation of the phenyl to an alkoxy arene compound;
h) oxidization of the 11-hydroxyl to an 11-ketone;
i) conversion of the 11-ketone to 11-trimethylsilylmethyl-n-alcohol;
j) conversion to the 11-methylene and removal of the protecting group at C-17 to yield the 17-ketone;
k) reduction of the 11-methylene to 11β-methyl;
l) reduction of the 17-ketone to 17β-hydroxyl;
m) conversion of the 3-alkoxy arene to a 4-en-3-one system.

The reagents generally required to effect the above transformations may be described using the same alphabetical system;
a) effected by use of an electronegatively-substituted quinone;
b) effected by using a methyllithium copper complex;
c) carried out using an electronegatively substituted quinone;
d) forming the ketal by acid-catalyzed reaction with a 1,2 or 1,3-diol;
e) carried out by using a complex metal hydride reagent;
f) carried out using a metal/arene mixture;
g) using an alkyl halide or activated alkylester, such as a sulfonate ester in the presence of a base;
h) carried out by using a chromium oxidant;
i) carried out by using a trialkyl silylmethyl organometallic reagent,
j) carried out by treatment with an acid;
k) carried out by using a metalalyzed hydrogenation;
l) carried out by using a complex metal hydride reagent; and
m) carried out by using a dissolving metal in an amine solvent, followed by treatment with an acid.

The above exemplary reaction will now be more specifically described below.

More specifically, the quinone of step a) is 2,3-dichloro-5,6-dicyanoquinone in the presence of anhydrous HCl and dioxane solvent;

the methyllithium copper complex of step b) is formed from methyllithium and the dimethyl sulphide complex of cuprous bromide;

the quinone of step c) is 2,3-dichloro-5,6-dicyanoquinone;

the diol of step d) is ethylene glycol and the acid is p-toluene sulphonic acid;

the complex metal hydride reagent of step e) is lithium tri(t-butoxy)aluminum hydride;

the metal/arene mixture of step f) is lithium/biphenyl/diphenylmethane;

the alkyl halide of step g) is methyl iodide and the base is potassium carbonate and the solvent is methanol;

the oxidant of step h) is pyridinium chromate;

the organometallic of step i) is trimethylsilylmethyl magnesium chloride;

the acid of step j) is hydrochloric acid;

the hydrogenation of step k) is carried out with hydrogen in the presence of rhodium on aluminum oxide as a catalyst;

the reduction of step l) is carried out with sodium borohydride;

the dissolving metal of step m) is lithium, the solvent is ammonia and the acid is hydrochloric acid.

Of course, the 17β-ester or ether compounds may be made using known esterification or etherification reactions, whereas the 3-oxime or -methoxime compounds may be prepared from the 3-keto compound using conventional reactions for the formation of oximes and methoximes.

As noted, the above reaction sequence uses known reagents and reaction steps. However, the reaction sequence of the present invention affords the present androgenic steroid compounds in high yield with excellent stereoselectivity. Of particular importance is the introduction of the 7α-group, such as methyl, prior to introduction of the 11β-group, such as methyl.

Conjugate methylation of 17β-acetoxy-11β-methylestra-4,6-dien-3-one with MeLi/CuBr/Me$_2$S gave a 7α-methyl:7β-methyl ratio of ca. 1:1, in contrast to the essentially complete 7α-methylation found in the absence of the 11β-methyl group. Thus, contrary to expectations based on potential steric hindrance of the β-side addition by the 11β-methyl, the 11β-methyl group enhanced 7β-methyl addition under these conditions. However, when the approach used for the method described here is followed, the 7α-methyl substituent is introduced with high stereoselectivity and later the 11β-methyl substituent is also introduced with high stereoselectivity.

For a general overview of steroid synthesis see *Organic Chemistry of Drug Synthesis*, Chapter 10 "Steroids" by D. Lednicer and L. A. Mitscher (Highly-Interscience 1977) and *Encyclopedia of Chemical Technology*, Vol. 22 "Steroids, pp 851-921 (Wiley-Interscience, 1997).

The Use of the Androgenic Steroid Compounds

The naturally occurring androgenic hormones are required for the development and maintenance of secondary sexual characteristics, libido and spermatogenesis. They also have anabolic properties, in promoting muscle growth and maintenance. Lower than normal levels of these hormones may occur as a result of aging or of other conditions. Hormone replacement therapy is then necessary to maintain energy, libido and lean body and bone mass at normal levels. The androgenie compounds of the present invention may be used in such therapy. Other conditions or treatments may also require the use of androgenic compounds. For example, one approach to male contraception entails the use of testosterone or esters thereof to suppress gonadotrophin production, thereby achieving azoospermia or oligospermia. Perhaps more practical in achieving azoospermia is the use of testosterone in combination with progestins, where the testosterone both contributes to the contraceptive effect and also replaces the otherwise suppressed endogeneous androgens. Administration of agonists or preferably antagonists of gonadotophin releasing hormone results in decreased sperm production, but also suppresses testosterone production. Thus, testosterone or other androgen must be given to make up the deficit. Antiestrogens also cause infertility in male animals. Their use may or may not require added androgen. Thus, androgens are useful in control of reproduction in the male, either alone or in conjunction with other agents such as those mentioned or other compounds. The androgenic steroids of the present invention may be used wherever a physical condition necessitates addition to or supplementation of endogenous androgenic hormones. Due to the enhanced potency of the present compounds as compared to testosterone, however, the former can be administered in much lower doses than the latter, which makes the administration of the present compounds much easier.

The androgenic steroid compounds of the present invention may be administered in any conventional manner, such as oral, buccal, intramuscular, subdermal implant, skin patch or even inhalation. These compounds may be administered by themselves or in combination with other active or inert ingredients as a composition.

When used as a composition, the androgenic steroid compounds of the present invention may be formulated in any conventional manner known to those skilled in the art for steroid compositions.

For example, the androgenic steroid compounds may be formulated as described in U.S. Pat. Nos. 3,828,106; 3,767,685; 3,658,789; and 3,441,559; all of which are incorporated herein in the entirety.

Accordingly, the present invention also provides compositions containing the present androgenic steroid compounds. Other therapeutic or reproductively active agents, such progestins, analogs of gonadotrophin releasing hormone, antiestrogens or other anabolic steroids may be included in these compositions or may be administered in conjunction with the present androgenic steroid compounds. Examples of progestins are levonorgestrel, cyproterone acetate (also an antiandrogen) and medroxyprogesterone acetate. Examples of gonadotrophin releasing hormone analogs are leuprolide acetate (agonist) and cetrorelix (antagonist). An example of an antiestrogen is 7α-(9-(4,4,5,5,5-pentafluoropentylsulfinyl)nonyl)estra-1,3,5(10)-triene-3, 17β-diol. Examples of other anabolic steroids are testosterone, oxandrolone, nandrolone and fluoxymesterone. However, any progestin, analog or gonadotrophin releasing hormone, antiestrogen or other anabolic steroid may be used in conjunction with the present steroids.

Of course, the 17β-ester or ether compounds may be made using known esterification or etherification reactions, whereas the 3-oxime or -methoxime compounds may be prepared from the 3-keto compound using conventional reactions.

Experimental Details for the Synthesis of 7α,11β-dimethyl-17β-hydroxyestr-4-en-3-one (7α,11β-dimethyl-19-nortestosterone)

The preferred method of synthesis of 7α,11β-dimethyl-19-nortestosterone is outlined in Chart A. The commercially available starting material adrenosterone (A-1) was smoothly transformed into the $\Delta^{4,6}$-dienone compound A-2 upon treatment with acidic 2,3-dichloro-5,6-dicyanoquinone (DDQ). Conjugate methylation of A-2 gave the desired 7α-methyl compound A-3. Treatment of A-3 with DDQ in the absence of acid provided the $\Delta^{1,4}$ compound A-4. Standard ketalization gave the 17-ketal A-5, which was reduced to the 11β-alcohol A-6 by treatment with lithium tri-t-butoxyaluminum hydride. Ring A aromatization proceeded smoothly upon treatment with diphenyl lithium to give the phenolic compound A-7. Methylation under standard conditions (MeI/K$_2$CO$_3$) gave the 3-methoxy compound A-8. In the $^1$H NMR spectrum, the appearance of the aromatic protons and disappearance of the 19-methyl protons together with the observation of a sharp singlet at 3.78 ppm for the 3-methoxy group clearly indicated that the product was the desired one. Oxidation of A-8 with pyridinium chlorochromate (PCC) provided 11-ketone A-9. The 11-ketone A-9 was treated with trimethylsilyl methylmagnesium chloride to afford the 11carbinol A-10, which was hydrolyzed to the 11-methylene compound A-11 in excellent yield. Catalytic hydrogenation of A-11 with rhodium as catalyst gave 11β-methyl compound A-12 as the sole product. After reduction with NaBH$_4$, the 17-alcohol A-13 was subjected to Birch reduction. The resulting dienol ether was hydrolyzed by acid treatment to afford 7α,11β-dimethyl-19-nortestosterone. Experimental details are given in the following paragraphs, with the following general procedures being used for all examples.

Melting points were determined on a Thomas Kofler Micro Hot Stage melting point apparatus and are corrected.

Electron impact mass spectra were recorded at 70 eV, proton magnetic resonance ($^1$H NMR) spectra were obtained at 100 MHz or 60 MHz with tetramethylsilane (TMS) as an internal standard and infrared (IR) spectra were recorded by means of a Perkin-Elmer 467 Grating Infrared Spectrophotometer. Ultraviolet (UV) data were obtained by a Cary 14 recording spectrophotometer, Gas-liquid chromatographic (GLC) analyses were performed using a 1.8 m column of 3.8% OV-17 on Chromosorb W AWS or a 1.8 m column of OV-17 (1%)/QF-1 (1%) on Varaport 30, column oven at 250° C., and helium carrier at 23–27 mL/min. A Waters 660 Solvent Programmer with 6000A Pumps, U6K Injector, and a Schoeffel GM 770/SF 770 Detector system were used for high-pressure liquid chromatography (HPLC). Analytical thin layer chromatography (TLC) was routinely used to monitor reactions with EM Reagent Silica Gel 60F-254 precoated TLC plates (0.25 mm thickness). Purifications on preparative plates were achieved on Analtech, Inc., Uniplate precoated thin layer chromatographic plates (1.0 mm thickness). ICN Pharmaceuticals prepared dry column silica gel was used for column chromatographic purifications as were EM pre-packed silica gel columns. The mention of specific instruments, instrument settings, and chromatographic media are for the purposes of example and are not intended to be limiting.

Androsta-4,6-diene-3,11,17-trione (A-2)

Adrenosterone (androst-4-ene-3,11,17-trione, A-1, 50 g, 166.7 mmol) was dissolved in dioxane (1200 mL, dry), which had been saturated with HCl gas at 10° C. under argon, and a chilled solution of 2,3-dichloro-5,6-dicyanoquinone (DDQ, 50 g, 220 mmol) in hydrogen chloride saturated dioxane (450 mL) was added slowly to the stirred solution. Solid dihydro-DDQ rapidly separated from the solution. After 1.5 h, the mixture was filtered through a sintered glass funnel, most of the dioxane was evaporated under reduced pressure and the residue was chromatographed over silica gel (1000 g) using chloroform as the eluting solvent. The light-yellowish material from evaporation of the eluate was 48.7 g of the dienone compound A-2: mp 237° C.; UV (MeOH) $\lambda_{max}$ 278 nm ($\epsilon$24,600); IR (CHCl$_3$) 1745 (17-C=O), 1705 (11-C=O) and 1650 (3-conjugated C=O) cm$^{-1}$; $^1$H NMR (CDCl$_3$) $\delta$0.92 (s, 3, 18-CH$_3$), 1.32 (s, 3, 19-CH$_3$), 5.63 (s, 1, 4-H) and 6.13 (s, 2, 6- and 7-H); m/z 298 (M$^+$).

7α-Methylandrost-4-ene-3,11,17-trione (A-3)

Dimethylsulfide/cuprous bromide complex (389.0 g, 1.89 mol) was suspended in anhydrous ether (1500 mL) containing dimethylsulfide (175 mL) under an argon atmosphere at 10° C. Methyllithium in ether (1.7 mol) was added dropwise until the last trace of yellow precipitate just dissolved. A solution of the diene A-2 (57.0 g, 191 mmol) in dry tetrahydrofuran (THF, 1250 mL) was added dropwise to the stirred solution at 10° C. After addition was completed, the reaction mixture was stirred at room temperature for 1 h and poured into an ice-cold saturated ammonium chloride solution (2000 mL). The product was extracted with ethyl acetate (4×500 mL). The combined extracts were washed with water (2×500 mL), dried over sodium sulfate, and evaporated to yield 79.9 g of crude Δ$^5$-product. Without purification, the crude product was dissolved in methanol (1000 mL) and was treated with 10% hydrochloric acid (100 mL). After the mixture was stirred at room temperature for 2.5 h, TLC indicated an essentially complete reaction. The mixture was poured into 5% (w/w) aqueous sodium bicarbonate solution (1000 mL) and extracted with ethyl acetate (4×500 mL). The combined extracts were washed with water (2×500 mL), dried over magnesium sulfate and concentrated to yield 66.4 g of crude product. Purification through modified column chromatography (1000 g of silica gel, chloroform) removed most of the color, and the compound was recrystallized from acetone to yield a combined total of 21.2 g (36% yield) of A-3 of ~95% purity by GLC: mp 235–237° C.; UV (MeOH) $\lambda_{max}$ 238 nm ($\epsilon$12,560); IR (CHCl$_3$) 1740 (17-C=O), 1708 (11-C=O) and 1665 (3-enone) cm-1; $^1$H NMR (CDCl$_3$) $\delta$5.71 (s, 1, 4-H), 1.40 (s, 3, 19-CH$_3$), 0.90 (d, 3, J=7 Hz, 7α-CH$_3$) 0.84 (s, 3, 18-CH$_3$); m/z 314 (M$^+$).

7α-Methylandrosta-1,4-diene-3,11,17-trione (A4)

To a solution of 7α-methyladrenosterone A-3, (20.7 g, 70.2 mmol) in 800 mL of freshly distilled benzene was added 20 g (78 mmol) of DDQ in one portion. The reddish solution was stirred under N$_2$ and refluxed for 20 h. Upon cooling, the dihydro-DDQ was filtered and washed with 150 mL of benzene. The filtrate and washings were combined and concentrated to a dark gummy foam which was chromatographed on a dry column of silica gel (1.2 kg), employing acetone-chloroform (1:19) as the solvent system. The desired fractions were combined and concentrated to afford 10.0 g (49% of theory) of the final product (A-4): mp 257–259° C.; UV (MeOH) $\lambda_{max}$ 238 nm ($\epsilon$13,500); IR (CHCl$_3$), 1742 (17-C=O), 1710 (11-C=O), 1662 (3-C=O) cm$^{-1}$; $^1$H NMR (CDCl$_3$) $\delta$7.6 (d, 1, J=10 Hz, 1-H), 6.1 (dd, 1, J=10, 1 Hz, 2-H), 6.05 (br s, 1, 4-H), 1.45 (s, 3, 19-CH$_3$), 0.9 (s, 3, 18-CH$_3$), 0.85 (d, 3, J=5 Hz, 7α-CH$_3$); m/z 312 (M$^+$).

17,17-Ethylenedioxy-7α-methylandrosta-1,4-diene-3,11-dione (A-5)

Into a 500-mL round bottom flask fitted with a Dean-Stark trap and condenser were added 2.8 g (9.0 mmol) of 7α-methyl-Δ$^1$-adrenosterone (A4) in 300 mL of dry toluene, 25 mL of ethylene glycol and 250 mg of p-toluenesulfonic acid monohydrate. The mixture was refluxed for 3 h and toluene was removed occasionally from the Dean-Stark trap. The reaction mixture was cooled to room temperature and diluted with water. The product was extracted with ether and chloroform. The combined extracts were washed with dilute NaHCO$_3$ (5% w/w) solution, dried over Na$_2$SO$_4$ (anhydrous) and concentrated to give 3.0 g of the crude reaction product, which was purified by dry column chromatography to afford 2.3 g (72% of theory) of the desired ketal A-5: mp 210–213° C.; UV (MeOH) $\lambda_{max}$ 238 nm ($\epsilon$13,100); IR (CHCl$_3$), 1705 (11-C=O), 1662 (3-C=O) cm$^{-1}$; $^1$H NMR (CDCl$_3$) $\delta$7.7 (d, 1, J=10 Hz, 1-H), 6.15 (dd, 1, J=10, 1 Hz, 2-H), 6.0 (br s, 1, 4-H), 3.8 (s, 4, 17-ketal) 1.45 (s, 3, 19-CH$_3$), 0.8 (s, 3, 18-CH$_3$), 0.78 (d, 3, J=6 Hz, 7α-CH$_3$); m/z 356 (M$^+$).

17,17-Ethlylenedioxy-11β-hydroxy-7α-methnylandrosta-1,4-dien-3-one (A-6)

Lithium tri-t-butoxyaluminum hydride (4.5 g, 17.2 mmol) was dissolved in 30 mL of freshly distilled tetrahydrofuran (THF). To this hydride solution at 0° C. was added a solution of A-5 (2.3 g, 6.9 mmol) in 25 mL of THF under N2 over a period of 1 h. The clear yellowish solution was stirred at 0° C. for 3 h. At this stage, TLC indicated only ⅓ of the starting material reacted. After the mixture was allowed to stir overnight, 2 mL of 5% (w/w) NaOH solution was added at 0° C. The cloudy mixture was stirred for an additional hour and the product was extracted with chloroform and washed with NaHCO$_3$. Removal of solvent gave 2.2 g of the crude reaction product which was purified by dry column chromatography (silica gel, 5% acetone-chloroform) to give 1.8 g (78% of theory) of the 11-OH compound A-6: mp 242–244° C., UV (MeOH) $\lambda_{max}$ 241 nm ($\epsilon$14,000); IR (CHCl$_3$), 1660 (3-C=O) cm$^{-1}$; $^1$H NMR (CDCl$_3$) $\delta$7.1 (d, 1, J=10 Hz, 1-H), 6.1 (dd, 1, J=10, 2 Hz, 2-H), 5.9 (br s, 1, 4-H), 4.5 (br, s, 1, 11α-H), 3.8 (s, 4, 17-ketal), 1.4 (s, 3, 19-Me), 1.1 (s, 3, 18-Me), 0.75 (d, 3, J=6 Hz, 7α-Me.

17,17-Ethylenedioxy-7α-methylestra-1,3,5(10)-triene-3,11β-diol (A-7)

Into a flame dried 250-mL three neck round bottom flask, fitted with condenser and addition funnel, were placed 2.5 g of biphenyl, 16 mL of diphenylmethane and 80 mL of freshly distilled tetrahydrofuran. The mixture was heated to reflux and ca. 0.5 g (71 mg-atom) of lithium wire was added in portions. Within 10 min, the characteristic dark blue-green color of the radical adduct appeared. The dark blue solution was refluxed with vigorous stirring for 30 min followed by dropwise addition over a period of 30 min of a solution of A-6 (1.85 g, 15.35 mmol) in 25 mL of tetrahydrofuran. The mixture was stirred at reflux for 15 min, then cooled to 0° C. and carefully decomposed with methanol and water. The solvent was removed in vacuo. The residue was taken up in ethyl acetate and chloroform and washed with 5% (w/w) NaHCO$_3$ solution. Evaporation of solvent afforded 4.5 g of the crude reaction product, which was purified by dry column chromatography (silica gel, 15% acetone-chloroform) to give 1.5 g (82% of theory) of the desired phenolic compound (A-7); mp 106–108° C.; UV (MeOH) $\lambda_{max}$280 (ε2100), 224 nm (6500); $^1$H-NMR (CDCl$_3$) δ7.05 (br d, 1, J=8 Hz, 1-H), 6.5 (br d, 1, J=8 Hz, 2-H), 6.45 (br s, 1, 4-H), 4.7 (br, s, 1, 11-H), 3.8 (br s, 4, 17-ketal), 1.1 (s, 3, 18-Me), 0.80 (d, 3, J=6 Hz, 7α-CH$_3$); m/z 344 (M$^+$).

17,17-Ethylenedioxy-3-methoxy-11β-hydroxy-7α-methylestra-1,3,5(10)-triene (A-8)

Into a 50-mL round bottom flask fitted with a condenser were added the phenolic compound A-7 (1.5 g, 14.4 mmol) in 25 mL of methanol and 5.0 g of potassium carbonate. Under vigorous stirring, methyl iodide (6.0 mL) was added dropwise over a period of 30 min. The mixture was refluxed under argon for 1.5 h. TLC indicated the reaction was complete. The solvent was removed under reduced pressure. After dilution with water, the product was extracted with ethyl acetate (3×) and dried over Na$_2$SO$_4$. Evaporation of the solvent gave 1.4 g (90% of theory) of the desired 3-methoxy compound A-8. The appearance of a sharp singlet around 3.8 ppm in the $^1$H NMR spectrum is indicative of the correct product.

3-Methoxy-17,17-ethylenedioxy-7α-methylestra-1,3,5(10)-triene-11-one (A-9)

Pyridinium chlorochromate (2.5 g, 11.6 mmol) was suspended in 25 mL of freshly distilled methylene chloride. A solution of the 11-hydroxy compound A-8 (1.4 g, 3.91 mmol) in 20 mL of CH$_2$Cl$_2$ was added slowly. The mixture was stirred at room temperature for 3 h. The mixture was poured into 100 mL of diethyl ether. The remaining black residue in the flask was rinsed with three 50 mL portions of ether. The ethereal solution and washings were combined, dried over Na$_2$SO$_4$ and concentrated to give 1.5 g of the crude reaction product which was further purified by dry column chromatography (silica gel, 5% acetone-chloroform) to afford 1.1 g (79% of theory) of the desired 11-keto compound A-9; mp 72–74° C.; IR (CHCl$_3$); 1705 (11-C=0), cm$^{-1}$; $^1$H NMR (CDCl$_3$) δ3.76 (s, 3, 3-OCH$_3$), 3.88 (br d, 4, 17-ketal), 0.90 (d, 3, J=6 Hz, 7α-CH$_3$), 0.88 (s, 3, 18-CH$_3$)$_x$; m/z 356 (M$^+$).

3-Methoxy-7α-methyl-11-methyleneestra-1,3,5(10)-triene-17-one (A-11)

A solution of 17 mL of chloromethyltrimethylsilane in 20 mL of dry diethyl ether was added dropwise to a suspension of magnesium turnings (1.6 g) in 15 mL of dry ether over about 1 h, keeping the reaction mixture just at reflux temperature without external heating. A solution of the 11-keto compound A-9 (1.2 g, 3.40 mmol) in 30 mL of dry diethyl ether was added slowly, and the reaction mixture was refluxed for 3 h. After cooling to room temperature, the mixture was poured into ice cold NH$_4$Cl solution (15% w/w). The product was extracted with ethyl acetate and chloroform. The combined extracts were washed with water, dried over Na$_2$SO$_4$ and concentrated to dryness. Without purification, the crude carbinol A-10 obtained was dissolved in 30 mL of acetone and treated with 10 mL of hydrochloric acid solution (10% w/w). The mixture was stirred at room temperature for 18 h. The product was extracted with ethyl acetate and ether. The combined extracts were washed with NaHCO$_3$ (5% w/w) solution, dried with Na$_2$SO$_4$ and concentrated to give 1.0 g, (95% of theory) of the 11-methylene compound A-11: mp 144–146° C.; IR (CHCl$_3$), 1740 (17-C=0), cm$^{-1}$; $^1$H NMR (CDCl$_3$) δ7.1 (br d, 1, J=10 Hz, 1-H), 6.65 (dd, 1, J=10, 1 Hz, 2-H), 6.5 (s, 1, 4-H), 4.9 (s, 2, 11-CH$_2$), 3.75 (s, 3, 3-OCH$_3$), 0.89 (s, 3, 18-CH$_3$) 0.84 (d, 3, J=6 Hz, 7α-CH$_3$); m/z 310 (M$^+$).

3-Methoxy-7α,11β-dimethylestra-1,3,5(10)-triene-17-one (A-12)

The 11-methylene compound A-11 (1.0 g, 3.22 mmol) was dissolved in 75 mL of dry ethyl acetate and was treated with 1.0 g of 5% rhodium-on-alumina catalyst. The mixture was stirred under one atmospheric pressure of hydrogen at room temperature for 18 h. The progress of the reaction was monitored by GLC using a 1.8 m, 3.8% OV-17 column. The catalyst was filtered off and the filtrate and washings were concentrated to give 1.00 g of the crude reaction product which was purified by dry column chromatography (silica gel, 5% acetone-chloroform) to afford 0.88 g (87% of theory) of the desired 11β-methyl compound A-12: mp 114–115° C.; IR (CHCl$_3$), 1740 (17-C=0), cm$^{-1}$; $^1$H NMR (CDCl$_3$) δ7.0 (br d, 1, J=10 Hz, 1-H), 6.6 (dd, 1, J=10, 2 Hz, 2-H), 6.5 (s, 1, 4-H), 0.95 (d, 3, J=4 Hz, 11β-CH$_3$), 0.92 (s, 3, 18-CH$_3$), 0.90 (d, 3, J=6 Hz, 7α-CH$_3$); m/z 312 (M$^+$).

3-Methoxy-17β-hydroxy-7α,11β-dimethylestra-1,3,5(10)-triene (A-13)

The 17-ketone A-12 (0.80 g, 2.56 mmol) in 50 mL of ethanol was treated with 0.6 g (18.2 mmol) of sodium borohydride at 0° C. The reaction was complete within 20 min, as indicated by TLC. Ethanol was removed under reduced pressure and the product was extracted with ethyl acetate and chloroform. The combined extracts were dried over sodium sulfate and concentrated to give 0.75 g (93% of theory) of white foam A-13: mp 130–131° C.; UV (MeOH) $\lambda_{max}$ 278 (ε1700), 288 (1510), 222 nm (6000); $^1$H NMR (CDCl$_3$) δ7.0 (d, 1, J=10 Hz, 1-H), 6.05 (dd, 1, J=10, 2 Hz, 2-H), 6.5 (s, 1, 4-H), 3.6 (m 1, 17-H), 0.9 (s, 3, 18-CH$_3$), 0.82 (d, 3 J=5 Hz, 11β-CH$_3$), 0.78 (d, 3, J=6 Hz, 7α-CH$_3$); m/z 314 (M$^+$).

7α,11β-dimethyl-19-nortestosterone (A-14, RTI-1176-012)

Liquid ammonia (150 mL) was condensed in a 500-mL round bottom flask equipped with a dry-ice-acetone condenser, dropping funnel and nitrogen inlet. To the vigorously stirred ammonia solution was added ca. 1.2 g (171 mg-atom) of lithium wire. The dark blue liquid ammonia and lithium complex solution was stirred at −78° C. for an additional hour. Steroid A-13 (0.75 g, 2.39 mmol) in 20 mL of freshly distilled tetrahydrofuran and 20 mL of t-butyl alcohol was added dropwise over a period of 20 min. The mixture was stirred at −78° C. for 3 h. A dark blue color persisted throughout the reaction period. Methanol was added cautiously until the dark blue color disappeared. The excess ammonia was evaporated under a stream of nitrogen.

The white residue was dissolved in water and the product was extracted from the aqueous phase with ethyl acetate and chloroform. The combined extracts were washed with water, dried over sodium sulfate and evaporated to give 0.72 g of the enol ether, which was dissolved in 50 mL of methanol and treated with 15 mL of 10% (w/w) hydrochloric acid solution. The mixture was warmed to 80° C. for 4 h. TLC showed a clean UV-quenching spot with lower Rf value than for starting material. The reaction mixture was poured over ice cold 5% (w/w) sodium bicarbonate solution and the product was taken up with ethyl acetate. The extracts were washed with water, dried over sodium sulfate and evaporated to give 0.70 g of the crude reaction product. Dry column chromatography and preparative TLC purification employing 5% acetone-chloroform as solvent system afforded 0.4 g (55% of theory) of final product A-14 (7α,11β-dimethyl-19-nortestosterone): mp 149–151° C.; UV (MeOH) $\lambda_{max}$ 242 nm (ε11,700); IR (CHCl$_3$), 3450 (17-OH), 1665 (3-enone) cm$^{-1}$; $^1$H NMR (CDCl$_3$), (100 MHz) δ5.86 (br, s, 1, 4-H), 3.63 (br t, 1, J=7 Hz, 17α-H), 1.08 (d, 3, J=7 Hz, 11β-CH$_3$),0.89 (s, 3, 18-CH$_3$), 0.7 (d, 3, J=7 Hz, 7α-CH$_3$); m/z 302 (M$^+$), high resolution MS: Found, 302.2243; calcd for $C_{20}H_{30}O_2$, m/z 302.2247.

EXAMPLE 2

Synthesis of 17β-Hydroxy-7α-methyl-11-methyleneestr-4-en-3-one (7α-methyl-11-methylene-19-nortestosterone)

3-Methoxy-7α-methyl-11-methyleneestr-1,3,5(10)-trien-17-one (A-11) was subjected to sodium borohydride reduction of the 17-ketone function, Birch reduction with lithium/NH$_3$(1), and acid hydrolysis and rearrangement to the title compound. Experimental details are as follows:

The 11-methylene ketone A-11 (100 mg, 0.28 mmol) in 8 mL of ethanol was treated with sodium borohydride (100 mg, 3.0 mmol) at 0° C. The reaction was complete in 20 min as indicated by TLC. Ethanol was removed under reduced pressure. The residue was diluted with water and the product was extracted from the aqueous phase with ethyl acetate and chloroform. The combined extracts were dried over sodium sulfate (anhydrous) and concentrated to give 105 mg of 17β-hydroxy-7α-methyl-11-methylene-3-methoxyestra-1,3,5(10)-triene ($^1$H NMR broad triplet at 3.80 ppm), used without further purification.

Liquid ammonia (20 mL) was condensed in a 25-mL round bottom flask equipped with a dry-ice-acetone condenser, dropping funnel and nitrogen inlet. To the vigorously stirred ammonia solution was added 0.3 g (43 mg-atom) of lithium wire. The dark blue complex solution was stirred at −78° C. for an additional hour. The above steroid (105 mg, 0.29 mmol) in 4 mL of freshly distilled THF and 3 mL of t-butyl alcohol was added dropwise and the mixture was stirred for an additional 3 h. A dark blue color persisted throughout the reaction period. Methanol was added cautiously until the dark blue color disappeared. The excess ammonia was evaporated under a slow stream of nitrogen. The white residue was dissolved in water and the product was extracted from the aqueous phase with ethyl acetate. The combined extracts were washed with water, dried over sodium sulfate and evaporated to give 100 mg of the crude reaction product. Without purification, the residue was dissolved in 15 mL of methanol and treated with 3 mL of 10% (v/v) hydrochloric acid/water. The mixture was heated to reflux for 2.5 h. TLC indicated complete reaction. Methanol was removed under reduced pressure. The light yellow residue was diluted with water and the product was extracted with ethyl acetate and chloroform. The combined extracts were washed with water, dried over sodium sulfate (anhydrous) and concentrated to afford 90 mg of the crude product. Preparative TLC purification (10% acetone in chloroform) afforded 37 mg of 17β-hydroxy-7α-methyl-11-methyleneestr-4-en-3-one (7α-methyl-11-methylene-19-nortestosterone): mp. 138–139° C.; IR (CHCl$_3$) 3500 (17-OH), 1668 (conjugated 3-ketone), (exocyclic C=C) 900 cm$^{-1}$; $^1$H NMR (CDCl$_3$) δ5.88 (br s, 1, 4-H), 4.8 (d, 2, 11-CH2), 3.80 (br t, 1, J=8 Hz, 17αH), 0.78 (d, 3, J=7 Hz, 7α-CH$_3$), 0.74 (s, 3, 18-CH$_3$); m/z 300 (M$^+$).

EXAMPLE 3

Synthesis of 7α,11β-dimethyl-17β-heptanoyloxyestr-4-en-3-one (7α,11β-dimethyl-19-nortestosterone enanthate)

7α,11β-dimethyl-17β-hydroxyestr-4-en-3-one A-14 (200 mg, 0.66 mmol) was dissolved in dry benzene (4 mL) and dry pyridine (1 mL). Under an argon atmosphere, freshly distilled heptanoyl chloride (1 mL) was added to the stirred solution at 0° C. The reaction was complete within 15 min as indicated by TLC. The reaction mixture was poured into water, neutralized with a 5% (w/w) aqueous sodium bicarbonate solution and extracted with ethyl acetate. The combined extracts were washed with water, dried over sodium sulfate (anhydrous) and concentrated to give 450 mg of yellowish oil that was purified by dry column chromatography (silica gel, 50 g, 5% acetone-chloroform) to afford 280 mg of the desired enanthate derivative: IR (CHCl$_3$) 1730 (enanthate C=O), 1668 (3-conjugated C=O); $^1$H NMR (CDCl$^3$, 100 MHz) δ5.85 (br s, 1, 4-H), 4.60 (br t, 1, 17α-H), 1.06 (d, 3, J=7 Hz, 11β-CH$_3$), 0.90 (s, 3, 18-CH$_3$), 0.77 (d, 3, J=7 Hz, 7α-CH$_3$); m/z 414 (M$^+$).

EXAMPLE 4

In order to demonstrate the importance of the 7α,11β-disubstitution of the present androgenic steroid compounds, a receptor binding study was conducted by evaluating relative binding (DHT=100) to androgen receptor from rat ventral prostate to obtain Androgen RBA.

Androgenic Activity was also evaluated using subcutaneous administration to immature castrated male rats (Testosterone=100).

Additionally, Estrogen RBA was determined by relative binding (Estradiol=100) to estrogen receptor from immature female rat uterus, while Estrogenic Activity was determined by subcutaneous administration to immature female rats (Estradiol=100).

The following compounds, defined by substituents on 19-nortestosterone, were tested.

| Compound # | 7α | 11β | Other |
|---|---|---|---|
| 1 | CH$_3$ | CH$_3$ | |
| 2 | CH$_3$ | H | |
| 3 | CH$_3$ | CH$_3$ | 5α-dihydro |
| 4 | CH$_3$ | CH$_2$= | |
| 5 | CH$_3$ | H | Δ-14 |
| 6 | CH$_3$ | CH$_3$ | Enanthate ester |
| 7 | H | H | 7β-methyl |

The results obtained are summarized in Tables 1 and 2 hereinbelow.

The importance of the 7α-methyl isomer and of its stereoselective synthesis is emphasized by the finding that 7α-methyl-19-nortestosterone has a relative binding activity (RBA) for the androgen receptor from rat of 162 compared to dihydrotestosterone (=100) versus an RBA value of 22 for 7β-methyl-19-nortestosterone. The further importance of the concomitant 11β-methyl group is shown by the androgenic RBA of 194 for 7α,11β-dimethyl-19-nortestosterone and the marked increase in acute androgenic activity of this compound as compared with 7α-methyl-19-nortesterone (see Table 1) and of the greater potency and longer duration of action of the enanthate ester of 7α,11β-dimethyl-19-nortestosterone as compared with testosterone enanthate (See Table 2).

aerosol form. When used in aerosol form, the compounds of the present invention may be used in compressed air or other gaseous medium suitable for nasal injection in a can or vial having spraying means, such as a nozzle, for releasing the contents. Such containing means and aerosol formulations for nasal administration are known in the art.

The compounds and/or compositions of the present invention when formulated for dermal application may be in the form of a cream, lotion or solution for facile topical application. In preparing the cream, lotion or solution, any

TABLE 1

Receptor Binding and Single Dose Activity

| Compound | Substituents on 19-nortestosterone[#] | | | | Androgenic Activity[##] | | | | |
|---|---|---|---|---|---|---|---|---|---|
| RTI No. | 7α | 11β | Other | Androgen RBA* | Seminal Vesicles | Ventral Prostate | Levator Ani | Estrogen RBA** | Estrogenic Activity[$] |
| 1176-012 | $CH_3$ | $CH_3$ | | 194 | 1540 (n = 3) | 1480 (n = 3) | 3800 (n = 3) | 0.6 (n = 3) | 0.8 |
|  |  |  |  | (n = 4) |  |  |  |  |  |
| 1176-013 | H | H | 7β-methyl | 22 (n = 2) |  |  |  |  |  |
| 1176-024 | $CH_3$ | H |  | 162 (n = 4) | 790 | 609 | 2510 |  |  |
| 1471-032 | $CH_3$ | $CH_3$ | 5-alpha-dihydro |  | 377 | 742 |  |  | 0.7 |
| 1471-034 | $CH_3$ | $CH_2$= |  | 176 | 993 | 1519–2148 |  |  |  |
| 1471-038 | H | $CH_3$ | delta-14 | 11 | 100*** | <100*** | 400*** |  |  |

[#]Estr-4-en-17β-o1-3-one
*Relative binding (Dihydrotestosterone = 100) to androgen receptor from rat ventral prostate
[##]Subcutaneous administration to immature castrated male rats (Testosterone = 100)
**Relative binding (Estradiol = 100) to estrogen receptor from immature female rat uterus
[$]Subcutaneous administration to immature female rats (Estradiol = 100)
***Single dose level study

TABLE 2

Long Term Androgenic Activity in Male Rats (% Change from Control)

| Compound | Substituents on 19-nortestosterone | | | Week after Dose | Final Body Weight (% change from control) | Seminal Vesicle Weight (% change from control) | Ventral Prostate Weight (% change from control) |
|---|---|---|---|---|---|---|---|
|  | 7α | 11β | Other |  |  |  |  |
| Testosterone enanthate (0.6 mg) |  |  | 10-$CH_3$-Enanthate ester | 1 | 0% | 452% | 409% |
|  |  |  |  | 2 | 6% | 318% | 339% |
|  |  |  |  | 4 | −7% | 281% | 291% |
|  |  |  |  | 6 | 0% | 248% | 405% |
|  |  |  |  | 8 | −6% | 187% | 150% |
|  |  |  |  | 10 | 0% | 179% | 130% |
| RTI 1471-029 (0.3 mg) | $CH_3$ | $CH_3$ | Enanthate ester | 1 | 9% | 571% | 368% |
|  |  |  |  | 2 | 1% | 580% | 582% |
|  |  |  |  | 4 | 3% | 438% | 583% |
|  |  |  |  | 6 | −1% | 603% | 649% |
|  |  |  |  | 8 | −10% | 312% | 340% |
|  |  |  |  | 10 | −2% | 426% | 562% |
| (0.6 mg) |  |  |  | 1 | 15% | 968% | 628% |
|  |  |  |  | 2 | 6% | 1428% | 778% |
|  |  |  |  | 4 | 1% | 1222% | 1145% |
|  |  |  |  | 6 | 0% | 1777% | 1810% |
|  |  |  |  | 8 | −16% | 1044% | 858% |
|  |  |  |  | 10 | 1% | 924% | 749% |

The compounds of the present invention may be used in any formulation which is suitable for administration by oral, buccal, nasal, intravenous, dermal, subdermal, intramuscular or rectal means. However, the present compounds may be advantageously used in smaller than conventional skin patches, in formulations for buccal administration or in conventional and dermatologically acceptable base formulation may be used.

For example, a base formulation may be prepared in accordance with any of U.S. Pat. Nos. 4,126,702; 4,760,096 or 4,849,425, all of which are incorporated herein by reference in the entirety.

The present compounds and/or compositions of the present invention may be used alone or in combination with one or more other pharmacologically active compound as noted above for hormone treatment of a mammal in either human or animal use.

Further, the present compounds and/or compositions of the present invention may also be used alone or in combination with progestins or gonodotrophin-releasing hormone analogs, either agonists or antagonists, in controlling male fertility. In either utility, the amount administered per dosage is generally from about 5% to about 125% of a conventional dosage of a conventional drug. The male may be a human or an animal, such as a cat, dog, pig, cow, sheep or ox.

In accordance with the present invention, while the dosages of the present compounds and/or compositions administered may be less than conventional dosages, the frequency of administration is generally less frequent to the same as for conventional steroids. However, the frequency of administration will depend upon various factors, such as age, weight, type of formulation, and other medication used, for example, under the guidance of a physician.

Having described the present invention, it will now be apparent to those skilled in the art that many changes and modifications may be made to the above-described embodiments without departing from the spirit and the scope of the present invention.

For example, it will be apparent to one skilled in the art that various modifications of the described synthetic route may be made, as long as one introduces the 7α-substituent prior to introduction of the 11-substituent. Thus, for example, the compound 3-methoxy-7α-methylestra-1,3,5 (10)-trien-17-one or the analogous 17β-ol or 17-acetate may be made by aromatization of the analogous 7α-methyltestosterone or 7α-methyl-19-nortestosterone derivative followed by 3-O-methylation. Oxidation of the benzylic 11-position and protection at C-17 would lead to compound 9 shown in the synthetic scheme (Chart A) above. Alternatively the aromatic compound may be converted by Birch reduction, hydrolysis, treatment with pyridinium perbromide and ketalization to a 3-ketal-5(10),9(11)-diene, which could be epoxidized at the 5(10)-position and further converted to the 11β-methyl-4-ene-3-one by reaction with an organocopper reagent, acid hydrolysis, double bond reduction and isomerization. It will also be apparent that various other functions and protecting groups may be used to preserve the desired 17-oxygenated substituent during the reaction sequence. These and other such modifications of the synthesis are explicitly within the scope of the present invention.

What is claimed as new and is desired to be secured by Letters Patent of the United States is:

1. A pharmaceutical composition, comprising:
   a) a pharmaceutically effective amount of 7α, 11β-dimethyl-17β-[[(trans-4-(n-butylI cyclohexyl) carbonyl]oxy]estr-4-en-3-one; and
   b) a pharmaceutically acceptable carrier.

2. The pharmaceutical composition of claim 1, which is suitable for injection.

3. A method of effecting hormonal treatment in a mammal, which comprises administering an effective amount of 7α, 11β-dimethyl- 17β[[(trans-4-(n-butyl) cyclohexyl)carbonyl]oxy]estr-4-en-3-one to a mammal in need thereof.

4. The method of claim 3, wherein the mammal is a male.

5. The method of claim 3, wherein the mammal is a male and the hormonal treatment is controlling male fertility.

6. The method of claim 5, further comprising administering a progestin.

7. The method of claim 3, wherein the hormonal treatment is promoting muscle maintenance.

8. A method of making 7α, 11β-dimethyl-17β[[(trans-4-(n-butyl) cyclohexyl)carbonyl]oxy]estr-4-en-3-one, comprising:

a) introducing a 6,7-double bond into adrenosterone;

b) effecting 1,6-addition of a methyl group by reaction with an organometallic reagent, followed by acid treatment;

c) introducing a 1,2-double bond;

d) protecting the 17-ketone functionality;

e) reducing the 11-ketone group to an 11-hydroxy group;

f) aromatizing the A-ring to a phenol;

g) alkylating the phenol ring to an alkoxy arene compound;

h) oxidizing the 11-hydroxyl to an 11-ketone;

i) converting the 11-ketone to 11-methylene;

j) removing the protecting group at C-17 to yield the ketone;

k) reducing the 11-methylene to 11β-methyl;

l) reducing the 17-ketone to 17β-hydroxyl; and m) converting the 3-alkoxy arene to a 4-en-3-one compound; and esterifying the 17β-hydroxyl.

9. An androgenic steroid represented by the formula:

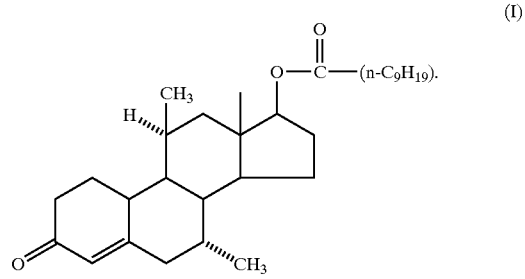

(I)

10. A pharmaceutical composition, comprising:
   a) a pharmaceutically effective amount of an androgenic steroid represented by the formula:

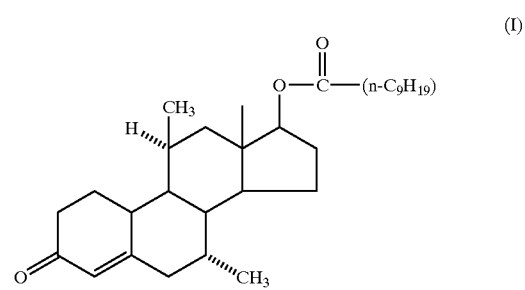

(I)

and b) a pharmaceutically acceptable carrier.

11. The pharmaceutical composition of claim 10, which is suitable for injection.

12. A method of effecting hormonal treatment in a mammal, which comprises administering an effective amount of an androgenic steroid represented by the formula:

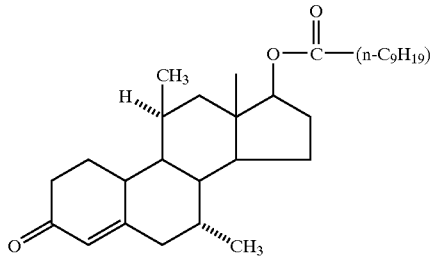

to a mammal in need thereof.

13. The method of claim 12, wherein the mammal is a male.

14. The method of claim 12, wherein the mammal is a male and the hormonal treatment is controlling male fertility.

15. The method of claim 14, further comprising administering a progestin.

16. The method of claim 12, wherein the hormonal treatment is promoting muscle maintenance.

17. A method of making an androgenic steroid represented by the formula:

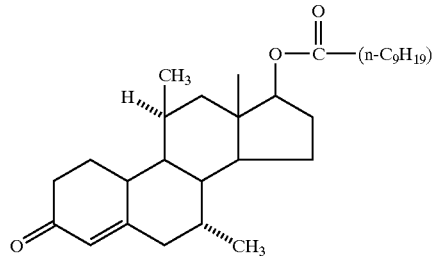

comprising:
a) introducing a 6,7-double bond into adrenosterone;
b) effecting 1,6-addition of a methyl group by reaction with an organometallic reagent, followed by acid treatment;
c) introducing a 1,2-double bond;
d) protecting the 17-ketone functionality;
e) reducing the 11-ketone group to an 11-hydroxy group;
f) aromatizing the A-ring to a phenol;
g) alkylating the phenol ring to an alkoxy arene compound;
h) oxidizing the 11-hydroxyl to an 11-ketone;
i) converting the 11-ketone to 11-methylene;
j) removing the protecting group at C-17 to yield the ketone;
k) reducing the 11-methylene to 11β-methyl;
l) reducing the 17-ketone to 17β-hydroxyl;
m) converting the 3-alkoxy arene to a 4-en-3-one compound; and
esterifying the 17β-hydroxyl.

* * * * *

UNITED STATES PATENT AND TRADEMARK OFFICE
CERTIFICATE OF CORRECTION

PATENT NO.    : 6,670,352 B2
DATED         : December 30, 2003
INVENTOR(S)   : C. Edgar Cook et al.

It is certified that error appears in the above-identified patent and that said Letters Patent is hereby corrected as shown below:

Column 2,
Line 15, "or Y-CH wherein" should read -- or Y-CH, wherein --.

Column 3,
Line 44-45, "or which is unsubstituted or substituted, and $R^7$ may be optionally substituted" should read -- or substituted; and $R^7$ is $C_6$-$C_{18}$ aryl or substituted aryl; or $R^7$ is a 5- to 15- membered heterocycle which is unsubstituted or substituted, and $R^7$ may be --;
Line 46, "OR9" should read -- $OR^9$ --.

Column 4,
Lines 52-54, "$C_2$-$C_{13}$ alkenyl or alkynyl which are optionally substituted; or $R^4$ is $C_4$-$C_{18}$ cycloalkyl or substituted cycloallyl; or" should read -- $C_2$-$C_{18}$ alkenyl or alkynyl which are optionally substituted; or $R^4$ is $C_4$-$C_{18}$ cycloalkyl or substituted cycloalkyl; or --.

Column 5,
Line 12, "or $C_2$-$C_{18}$, alkenyl" should read -- or $C_2$-$C_{18}$ alkenyl --;
Line 19, "$(CH_2)_{2\text{-}CH3}$" should read -- $(CH_2)_2$-$CH_3$ --;
Line 21, "-$CH_2$C=C-" should read -- -$CH_2$-C=C- --.

Column 8,
Line 31, "metalalyzed" should read -- metal-catalyzed --.

Column 10,
Line 56, "11carbinol" should read -- 11-carbinol --.

Column 12,
Line 50, "Ethylenedioxy-11β-hydroxy-7α-methnylandrosta-1" should read
-- Ethylenedioxy-11β-hydroxy-7α-methylandrosta-1 --.

Column 16,
Line 29, "$CDC1^3$" should read -- $CDC1_3$ --.

Column 19,
Line 55, "[(trans-4-(n-butylI" should read -- [(trans-4-(n-butyl) --.

UNITED STATES PATENT AND TRADEMARK OFFICE
CERTIFICATE OF CORRECTION

PATENT NO.    : 6,670,352 B2
DATED         : December 30, 2003
INVENTOR(S)   : C. Edgar Cook et al.

It is certified that error appears in the above-identified patent and that said Letters Patent is hereby corrected as shown below:

Column 20,
Line 5, "17β[[" should read -- 17β-[[ --.

Signed and Sealed this

Twelfth Day of October, 2004

JON W. DUDAS
*Director of the United States Patent and Trademark Office*